United States Patent [19]

Nyström et al.

[11] Patent Number: 5,659,071

[45] Date of Patent: Aug. 19, 1997

[54] PROCESS FOR THE PRODUCTION OF AMINOALKYLGUANIDINES

[75] Inventors: Jan-Erik Nyström, Kista; Hans Fredrik Sjöbom, Södertälje, both of Sweden

[73] Assignee: Astra Aktiebolag, Sodertalje, Sweden

[21] Appl. No.: 244,924

[22] PCT Filed: Jun. 1, 1994

[86] PCT No.: PCT/SE94/00517

§ 371 Date: Jun. 28, 1994

§ 102(e) Date: Jun. 28, 1994

[87] PCT Pub. No.: WO94/29269

PCT Pub. Date: Dec. 22, 1994

[30] Foreign Application Priority Data

Jun. 3, 1993 [SE] Sweden .................................. 9301912

[51] Int. Cl.$^6$ ................................................ C07C 261/00
[52] U.S. Cl. ................................................ 560/159
[58] Field of Search ........................ 560/159; 548/375.1

[56] References Cited

U.S. PATENT DOCUMENTS

| | | | |
|---|---|---|---|
| 4,346,078 | 8/1982 | Sandor et al. | 424/177 |
| 4,387,049 | 6/1983 | Pfeiffer | 260/112.5 |
| 5,498,724 | 3/1996 | Nystrom | 548/375.1 |

FOREIGN PATENT DOCUMENTS

| | | |
|---|---|---|
| 0277626 | 8/1988 | European Pat. Off. . |
| 2294699 | 7/1976 | France . |
| 463576 | 7/1928 | Germany . |
| 3222342 | 12/1983 | Germany . |
| 2085444 | 4/1982 | United Kingdom . |
| 93/1152 | 6/1993 | WIPO . |

OTHER PUBLICATIONS

Tian et al., Int. J. Peptide Protein Res. 37: pp. 425–429 (1991).
Mattingly, P., Synthesis pp. 366–368 (Apr. 1990).
Rzeszotarska et al., Org. Prep. and Proc. Int. vol. 20, No. 5: pp. 427–464 (1988).
Hegarty et al., Chemical Society, Perkin transactions II, vol. 15: pp. 2054–2060 (1973).
Greene, "Protective Groups in Organic Synthesis", pp. 218–287 1981.

*Primary Examiner*—Michael L. Shippen
*Attorney, Agent, or Firm*—Nixon & Vanderhye

[57] ABSTRACT

A process for the production of guanidino protected ω-aminoalkyl guanidines comprising reacting a diamine selectively at one amino group with an alkoxycarbonyl or aralkoxycarbonyl protected electrophilic guanylation reagent. The process of the invention is general and may be performed efficiently in one step yielding a product with high purity and in useful yields. The invention further refers to some compounds that are novel per se and to some novel compounds useful in the process of the invention.

22 Claims, No Drawings

PROCESS FOR THE PRODUCTION OF AMINOALKYLGUANIDINES

FIELD OF THE INVENTION

The present invention relates to a process for the production of guanidino protected aminoalkyl guanidines, especially alkoxycarbonyl or aralkoxycarbonyl protected ω-aminoalkyl guanidines, such as N-t-butoxycarbonyl-N'-(ω-aminoalkyl) guanidines and N-benzyloxycarbonyl-N'-(ω-aminoalkyl) guanidines. Representatives of this group of compounds are useful or potentially useful as peptide building blocks as mimics to the arginine residue. In particular the invention relates to a novel, one step process comprising reacting a diamine selectively at one amino-group with an alkoxycarbonyl or aralkoxycarbonyl protected electrophilic guanylation reagent. More specifically, the invention relates to a process reacting a symmetric 1,n-diamino alkane with a alkoxycarbonyl or aralkoxycarbonyl isourea or isothiourea giving an guanidino protected ω-aminoalkyl guanidine. The invention further relates to some compounds that are novel compounds per se. These novel compounds were produced by using the process of the invention. Furthermore the invention relates to some novel compounds, useful in the process of the invention.

BACKGROUND OF THE INVENTION

Protected guanidines having an important role in the synthesis of peptides having arginine residues. Various mimics to arginine have been used as peptide building blocks. From a synthetical and commercial point of view, arginine-mimics having a simplified structure compared to arginine are of particular interest. Perhaps the most attractive structural simplification of arginine is replacing the carboxylic group in arginine with a hydrogen giving a non-chiral molecule. The most important arginine derivatives in this context are noragmatine (N-(3-aminopropyl)-guanidine) and agmatine (N-(4-aminobutyl)-guanidine). More generally, ω-aminoalkyl guanidines of varying chain length are interesting as peptide building blocks, particularly as a substitute for an arginine terminus in a peptide.

Previously known examples of applications of peptide building blocks, of the general type —NH—C(=NH)—NH—[CH$_2$]$_n$—NH— are, see for example:

U.S. Pat. No. 4,387,049 disclosing example where n=3 (noragmatine), and

U.S. Pat. No. 4,346,078 disclosing example where n=4 (agmatine).

A free guanidino group [—NH—C(=NH)—NH$_2$] provides synthetic complications and to be synthetically useful the building block requires a protective group (PC) which may be removed from the guanidino group at a desired stage of the synthesis.

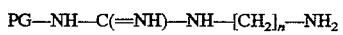

Frequently used protective groups for the guanidino group in arginine are for example alkoxycarbonyls such as t-butoxycarbonyl (Boc) and aralkoxycarbonyls such as benzyloxycarbonyl (Z). See for example: Wünsch E. "Methoden der Organischen Chemie (Houben Weyl), Syntheses yon Peptiden", 1974, 15/1, 506 ff. and Rzeszotarska Masiukiewicz Org. Prep. Proc. Int. 1988, 20, 427 ff. The expressions Boc and Z are used in the following description as abbreviates for t-butoxycarbonyl and benzyloxycarbonyl, respectively.

Guanidino protected ω-aminoalkyl guanidines, PG$_2$—NH—C(=NH)—NH—[CH$_2$]$_n$—NH$_2$ (3), are generally prepared starting from a mono-protected diaminoalkane (1) in which the free amino group is reacted with an electrophilic guanylation reagent, HN=C(L)—NH$_2$ where L is a leaving group, commonly used in guanidine syntheses. The reaction produces an amino protected ω-aminoalkyl guanidine (2) which after protection of the guanidino group with a second protective group (PG$_2$) and deprotection of the amino protective group (PG$_1$) gives the desired PG$_2$—NH—C(=NH)—NH—[CH$_2$]$_n$—NH$_2$ (3). In this method the protective groups have to be orthogonal. Examples of guanylation reagents that may be used are L=OMe, SMe, pyrazol-1-yl, 3,5-dimethyl-pyrazo-1-yl, and SO$_3$H. Recent developments have proposed introduction of the second protective group, PG$_2$, in the guanylation reagent. Such a method simplifies the linear synthesis and shortens it with one step, (1⇒3), see scheme 1.

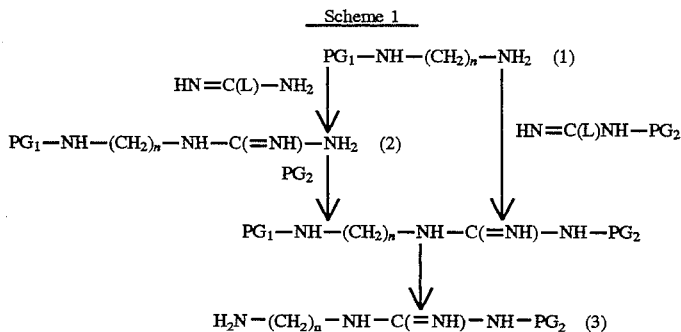

Scheme 1

Previously proposed guanylation reagents [PG$_2$—NH—C(L)=NH], carrying a protective group useful in guanidine syntheses, i.e. used to create a guanidino group, are disclosed in the following list:

for L/PG$_2$:

3,5-dimethyl-pyrazo-1-yl/NO$_2$ and 3,5-dimethyl-pyrazo-1-yl/tosyl; MeS/NO$_2$;

MeS/tosyl (See for example: Int. J. Peptide Res. 1991, 37, 425);

MeO/benzyloxycarbonyl (See for example: DE 3222342 A1);

MeS/benzyloxycarbonyl (See for example GB 2085444 A.

The mono protected diamine is generally prepared from the corresponding amino alcohol according to the four-steps protocol shown in scheme 2, (See for example Mattingly Synthesis 1990, 366).

Scheme 2

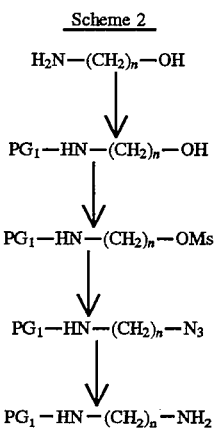

Consequently, methods previously known in the art totally require 6 to 7 synthetic steps in order to prepare a guanidino protected ω-aminoalkyl guanidine, $PG_2$—NH—C(=NH)—NH—$[CH_2]_n$—$NH_2$ (3). See scheme 1 in combination with scheme 2. Such compounds, where the protective group (PC) is a alkoxycarbonyl or aralkoxycarbonyl, such as for example t-butoxycarbonyl or benzyloxycarbonyl, can now be produced more efficiently in the one step synthesis using the process of the present invention.

BRIEF DESCRIPTION OF THE INVENTION

The present invention may be considered as an improvement over processes known in the art for the preparation of aminoalkyl guanidines. Furthermore, the process of the invention contributes to the art of desymmetrization of symmetric substrates, more specifically to the art of desymmetrization of symmetric diamines. The present invention provides a novel and efficient process for the production of a guanidino protected ω-aminoalkyl guanidine of the general formula RO—C(O)—NH—C(=NH)—NH—$C_nH_{2n}$—$NH_2$ (III) or its tautomer R—O—C(O)—N=C($NH_2$)—NH—$C_nH_{2n}$—$NH_2$ or a salt of one of these, where R is an alkyl or aralkyl group and n is an integer 2 to 18. R is preferably a residue promoting a crystalline product. More specifically, the process comprises reacting a symmetric primary 1,n-diaminoalkane (I) and a guanylation reagent (II) carrying a protective group yielding the protected ω-aminoalkyl guanidine (III) in one step, see scheme 3.

Scheme 3

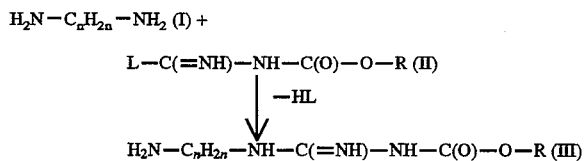

DETAILED DESCRIPTION OF THE INVENTION

The present invention is explained in detail in the following and especially by the accompanying examples. In a preferred embodiment of the process of the invention, the diamine (I) may be selected from 1,n-diamines of the general formula $NH_2$—$C_nH_{2n}$—$NH_2$, where —$C_nH_{2n}$— is a linear or branched alkyl group and n is an integer 2–18, preferably a linear alkyl group where n is 2–12, and especially where n is 2–5, 8 or 12. The guanylation reagent may be selected from a group of compounds of the general formula ROC(O)—N=C(L)—$NH_2$ (II) or its tautomer ROC(O)—NH—C(L)=NH or a salt of one of these. R is selected from the group consisting of a linear or branched $C_1$–$C_{12}$-alkyl group, preferably an alkyl group of 1–4 carbons such as methyl, ethyl, linear or branched propyl and butyl, preferably t-butyl, and an aralkyl group such as benzyl or substituted benzyl, preferably benzyl. L is a leaving group, which is useful in a guanylation reaction such as $R^2O$, $R^2S$, pyrazolyl, and substituted pyrazolyl, preferably 3,5-dimethyl-pyrazolyl, where $R^2$ is a lower alkyl, preferably a linear alkyl chain with 1–4 carbon atoms, methyl and ethyl are preferred.

The reaction may be performed in the presence or in the absence of a solvent, preferably the reaction is performed in the absence of a solvent. If a solvent is used said solvent can be: an aromatic hydrocarbon, such as an alkylbenzene and more specifically toluene or xylene; a hydrocarbon being linear or branched, cyclic or acyclic such as hexane, heptane, or cyclohexane; an alkyl nitril such as acetonitril; an alcohol such as isopropanol; or water.

There are two amino groups in the diamine, which may be guanylated. To suppress the side reaction where both amino groups are guanylated, the process is performed with about at least a stoichiometric amount of the diamine reactant in relation to the guanylation reagent, preferably employing an excess of the diamine reactant. The reaction can be performed with about 1–10 mol-equivalents, or preferably 1.5–6 equivalents, or most preferably 2–4 equivalents of the diamine reactant in relation to the guanylation reagent.

According to the process of the invention, the reactants and the solvent can be added to the reaction vessel in an arbitrary order at a suitable temperature, preferably the reactants and optionally the solvent(s) are mixed at ambient temperature. The reaction may be performed at about 20°–80° C., preferably at 40°–60° C. The reaction time is about 1–60 h, preferably 2–48 h. Upon prolonged reaction time the guanidino-protected aminoalkyl guanidine, produced from diamines where n=2, 3, or 4, i.e. diamino ethane, diamino propane or diamino butane, can undergo an intramolecular cyclization forming a 5, 6, and 7-membered cyclic guanidine as a by-product. Consequently, reactions with these amines should be stopped when about 80–98%, or preferably about 85–95%, or most preferably when about 90–95% of the guanylation reagent is consumed. The reaction is easily monitored by TLC or HPLC, see the accompanying examples.

An important advantage of the process of the invention is the isolation of the guanidino protected aminoalkyl guanidine by crystallization (precipitation). According to the present invention, crystallization can occur as the product is formed or as a subsequent step after the reaction is complete by trituration with a suitable solvent or solvent mixture, preferably an hydrocarbon such as heptane. The crystallization can occur in the presence or in the absence of the uureacted amine, most preferably in the presence of the unreacted diamine. Unreacted amine can be removed prior to the crystallization by vacuum distillation.

Another important advantage of the invention is the high volume efficiency with which the process can produce the product, particular when using the solvent free protocol whereby a reaction mixture of 300 mL yields about 100 g of product.

The guanylation reagents are prepared by acylation of O- or S-alkylisourea or 3,5-dimethylpyrazol formamidinium nitrate using previously known methods or modifications thereof, see references cited above. Some of the guanylation reagents used in the process of the invention are novel compounds per se.

According to the process of the invention, the guanidino-protected aminoalkyl guanidine is crystallized as the free base yielding the pure crude product by for instance filtration or centrifugation. The product is, if necessary, purified by recrystallization by dissolution in a polar solvent such as an alcohol, for example methanol, followed by trituration with an unpolar solvent such a hydrocarbon or an alkylbenzene such as toluene or xylene. The product may optionally be precipitated and purified as a salt with a suitable acid, such as hydrochloric acid.

In order to illustrate but not to limit the nature of the invention and the manner of practicing the same the following examples are presented. The reactions were monitored by TLC [silica, methylene chloride/ethanol/ammonium hydroxide (aq, 25%)=85/15/4] visualizing by either UV (254 nm) or iodine; or by HPLC (UV, 210 nm) using a silica column (Merck, RP select B) eluting with 30% acetonitril, 70% aqueous $NH_4H_2PO_4$ (50 mM, pH=3). NMR-spectra were recorded on a 200 MHz Bruker FT-spectrometer and the shifts (d) are reported in ppm down field of tetramethylsilane (TMS).

EXAMPLES

Preparation of N-(3-Aminopropyl)-N'-Benzyloxycarbonyl Guanidine (IIIa)

Example 1

To a 1000 mL round-bottomed flask was added N-benzyloxycarbonyl-O-methyl-isourea (II-OMe) (150 g, 0.72 mol), toluene (450 mL, 0.62 mL/mmol) and 1,3-diamino propane (Ia) (150 mL, 1.8 mol). The reaction mixture was heated to 30°–40° C. and stirred for 7 h followed by stirring at room temperature over night. Toluene (200 mL) was added and after 20 minutes stirring at room temperature the crystals were collected by filtration. The white crystalline product was washed with toluene (4×200 mL) and dried (vacuum, 30°–35° C., 8 h). The yield of N-(3-aminopropyl)-N'-benzyloxycarbonyl guanidine (IIIa) was 118 g (65% in theory). 1H NMR (1M DCl/D2O): 7.28 (5H, Ph), 5.11 (2H, s, $OCH_2Ph$), 3.28 (2H, t, $CH_2N$—C), 2.92 (2H, s, $CH_2NH_2$), 1.86 (2H, q, C—$CH_2$—C). Mp: 103°–105° C.

Example 2

To a 10 mL round-bottomed flask was added N-benzyloxycarbonyl-S-methyl-isothiourea (II-SMe) (0.45 g, 2.0 mmol), toluene (3.5 mL) and 1,3-diamino propane (Ia) (0.22 g, 3.0 mmol). The reaction mixture was heated to 40° C. and stirred for 9 h followed by stirring at room temperature over night. The white crystalline product was collected by filtration, washed with toluene (2×1 mL), and dried (vacuum, 30°–35° C., 4 h). The yield of N-(3-aminopropyl)-N'-benzyloxycarbonyl guanidine (IIIa) was 0.37 g (74% in theory).

Example 3

N-Benzyloxycarbonyl-1-[3,5-dimethylpyrazolyl] formamidine (II-pyr) (0.55 g, 2.0 mmol) and 1,3-diamino propane (Ia) (0.37 g, 5.0 mmol) was stirred in toluene (3.5 mL) at 40° C. for 5 h followed by stirring at room temperature for 1 h. Filtration, washing with toluene (2×1 mL), and drying (35° C., 15 mbar, 2 h) afforded 0.31 g (62%) of IIIa as a white crystalline product.

Example 4

The method in Example 2 was applied but toluene was replaced with xylene (3.5 mL/2 mmol II-SMe) and 1.5 equiv. of diaminopropane (Ia) was employed. The reaction mixture was stirred for 8 h at 60° C. and over night at 25° C. Filtration, washing (xylene), and drying gave 0.35 g (70%) of IIIa.

Example 5

The method in Example 1 was applied but toluene was replaced with xylene (3.5 mL/2 mmol II-OMe) and 4 equiv. of diaminopropane (Ia) was employed. The reaction mixture was stirred at 40° C. for 12 h and at 25° C. for 3 h. Filtration, washing (toluene), and drying gave 0.31 g (62%) of IIIa.

Example 6

The method in Example 1 was applied but toluene was replaced with n-hexane (3.5 mL/2 mmol II-OMe) and 2.0 equiv. of diaminopropane (Ia) was employed. The reaction mixture was stirred at 40° C. for 2 h and at 25° C. for 1 h. Filtration, washing (hexane), and drying gave 0.45 g (85%) of IIIa.

Example 7

The method in Example 1 was applied but toluene was replaced with cyclo-hexane (3.5 mL/2 mmol II-OMe) and 2.0 equiv. of diaminopropane (Ia) was employed. The reaction mixture was stirred at 40° C. for 3 h and at 25° C. for 0.5 h. Filtration, washing (cyclo-hexane), and drying gave 0.45 g (85%) of IIIa.

Example 8

The method in Example 1 was applied but toluene was replaced with acetonitrile (3.5 mL/2 mmol II-OMe) and 2.0 equiv. of diaminopropane (Ia) was employed. The reaction mixture was stirred at 40° C. for 2 h, at 25° C. for 1 h, and at 0° C. for 0.5 h. Filtration, washing (acetonitrile), and drying gave 0.09 g (18%) of IIIa.

Example 9

N'-Benzyloxycarbonyl-O-methyl-isourea (0.42 g, 2.0 mmol) and 1,3-diaminopropane (Ia) (0.37 g, 5.0 mmol) were allowed to react in isopropanol (1 mL) at 40° C. After stirring for 7 h n-hexane (3.5 mL) was added and the reaction mixture was stirred for 0.5 h at 25° C. followed by filtration. The crystals were washed with hexane (2×1 mL) and dried to give 0.35 g (70%) of IIIa.

Example 10

A mixture of N-benzyloxycarbonyl-O-methyl-isourea (II-OMe) (10.0 g, 0.048 mol) and 1,3-diaminopropane (Ia) (17.8 g, 0.240 mol) was stirred at 20° C. for 18 h and at 0° C. for 0.5 h. The crystalline product was collected by filtration, washed with toluene (4×15 mL), and vacuum dried (35° C., 3 h) to afford 8.2 g (68%) of white crystals of (IIIa).

Example 11

A mixture of II-OMe (0.42 g, 2.0 mmol) and Ia (0.88 g, 12 mmol) was stirred at 40° C. for 2.5 h and at 25° C. for 1 h followed by addition of toluene (3.5 mL). After the reaction mixture had been stirred for 1 h for the crystals were collected by filtration, washed with toluene (2×1 mL), and dried (35° C., 15 mm Hg, 16 h). The yield was 0.21 g (42%) of IIIa.

Example 12

A mixture of N-benzyloxycarbonyl-O-ethyl-isourea (II-OEt) (0.16 g, 0.7 mmol), toluene (1.3 mL) and 1,3-diaminopropane (Ia) (0.13 g, 1.7 mmol) was stirred at 40° C. for 8 h and at room temperature for 48 h. The crystalline product was collected by filtration, washed with toluene (2×1 mL), and vacuum dried (35° C., 2 h) to afford 0.09 g (51%) of white crystals of IIIa.

Purification of N-(3-Aminopropyl)-N'-Benzyloxycarbonyl Guanidine

Example 13

N-(3-Aminopropyl)-N'-benzyloxycarbonyl guanidine (IIIa) (1.0 g) was dissolved in MeOH (3 mL) and toluene (10 mL) was added. The reaction mixture was reduced (to approx. 50%) under vacuum and cooled for 1 h. The crystals were collected by filtration and vacuum dried. The yield of IIIa was 0.89 g (89%).

Example 14

To a stirred solution of N-(3-aminopropyl)-N'-benzyloxycarbonyl guanidine (IIIa) (4.0 g, 16.0 mmol), 2-propanol (22 mL) and methanol (9 mL) at room temperature was added over a 30 minute period HCl/2-propanol, 5M, (13 mL, 64 mmol). The reaction mixture was stirred at ambient temperature for 30 minutes. N-(3-Aminopropyl)-N'-benzyloxycarbonyl guanidine dihydrochloride (approximately 2 mg) was added whereby precipitation occurs immediately. The reaction mixture was stirred at ambient temperature for 2 h followed by stirring at 5° C. for 1.5 h. The crystalline product was collected by filtration, washed with 2-propanol/methanol=6/1 (2×10 mL), and vacuum dried (35° C., 2 h) to afford 4.26 g (82%) of white crystals of N-(3-aminopropyl)-N'-benzyloxycarbonyl guanidine dihydrochloride (IIIa×2 HCl).

Preparation of N-(4-Aminobutyl)-N'-Benzyloxycarbonyl Guanidine (IIIb)

Example 15

A mixture of N-benzyloxycarbonyl-O-methyl-isourea (II-OMe) (0.42 g, 2.0 mmol), toluene (3.5 mL) and 1,4-diamino butane (Ib) (0.26 g, 3.0 mmol) was stirred at 60° C. for 20 h, at 25° C. for 1.5 h, and at 0° C. for 2 h. The white crystalline product was filtered off, washed with toluene (2×1 mL), and dried (vacuum, 30°–35° C., 2.5 h). The yield of N-(4-aminobutyl)-N'-benzyloxycarbonyl guanidine (IIIb) was 0.36 g (68% in theory).

1H NMR (1M DCL/D$_2$O): 7.28 (5H, Ph), 5.10 (OCH$_2$Ph), 3.20 (2H, t, CH$_2$N—C), 2.87 (2H, t, CH$_2$—NH$_2$), 1.4–1.6 (4H, C—CH$_2$CH$_2$—C). Mp=110°–111° C.

Example 16

A mixture of N-benzyloxycarbonyl-S-methyl-isothiourea (II-SMe) (0.45 g, 2.0 mmol), toluene (3.5 mL) and 1,4-diamino butane (Ib) (0.26 g, 3.0 mmol) was stirred at 40° C. for 20 h and at 25° C. for 12 h. The white crystalline product was filtered off, washed with toluene (2×1 mL), and dried (vacuum, 30°–35° C., 2 h). The yield of N-(4-aminobutyl)-N'-benzyloxycarbonyl guanidine (IIIb) was 0.24 g (45% in theory).

Example 17

The method from example 15 was applied but toluene was replaced with xylene and the reaction mixture was stirred at 40° C. for 26 h and at 25° C. for 5 h. Filtration, washing (xylene), and drying gave 0.36 g (68%) of IIIb.

Example 18

The method from example 15 was applied but the reaction was carried out neat (no solvent) and 6 equiv. of diaminobutane (Ib) was used. The reaction mixture was stirred at 40° C. for 2 h and at 0° C. for 1 h. Filtration, washing (4×1 mL toluene), and drying gave 0.18 g (68%) of IIIb.

Preparation of Different Compounds of the Formula III

Example 19. N-(2-Aminoethyl)-N'-Benzyloxycarbonyl Guanidine

A mixture of N-benzyloxycarbonyl-O-methyl-isourea (II-OMe) (0.42 g, 2.0 mmol) and 1,2-diaminoethane (Ic) (0.72 g, 12 mmol) was stirred at 40° C. for 3 h and at 25° C. for 1 h. The crystals were collected by filtration. The white crystalline product was washed with toluene (4×1 mL) and dried (vacuum, 30°–35° C., 2 h). The yield of N-(2-aminoethyl)-N'-benzyloxycarbonyl guanidine IIIc was 0.28 g (60% in theory).

1H NMR (1M DCl/D$_2$O): 7.28 (5H, Ph), 5.11 (2H, s, OCH$_2$Ph), 3.54 (2H, t, CHN—C), 3.13 (2H, t, CH$_2$NH$_2$). Mp: 106°–113° C.

Example 20. N-(2-Aminoethyl)-N'-Benzyloxycarbonyl Guanidine

The method in Example 19 was applied but 2.5 equiv. of diaminoethane was used and the reaction was carried out in toluene (3.5 mL/2 mmol II-OMe). The reaction mixture was stirred 40° C. for 23 h and 25° C. for 1 h and then filtered. Washing and drying afforded 0.32 g (68%) of IIIc.

Example 21. N-(5-Aminopentyl)-N'-Benzyloxycarbonyl Guanidine

A mixture of N-benzyloxycarbonyl-O-methyl-isourea (II-OMe) (0.42 g, 2.0 mmol), toluene (3.5 mL) and 1,5-diaminopentane (0.50, 5.0 mmol) was stirred at 40° C. and for 48 h. The reaction mixture was concentrated under vacuum (35° C., 0.3 mbar) to give a crude product which was crystallized by addition of toluene followed by additon of heptane. The yield of N-(5-aminopentyl)-N'-benzyloxycarbonyl guanidine (IIId) was 0.3 g (60% in theory).

1H NMR (CDCl$_3$): 7.3 (5H, Ph), 5.04 (2H, s, OCH$_2$Ph), 3.16 (2H, t, CH$_2$N—C), 2.62 (2H, t, CH$_2$NH$_2$), 1.3–1.4 (6H, m).

Example 22. N-(8-Aminooctyl)-N'-Benzyloxycarbonyl Guanidine

A mixture of N-benzyloxycarbonyl-O-methyl-isourea (II-OMe) (0.42 g, 2.0 mmol) and 1,8-diaminooctane (Ie) (0.72 g, 12 mmol) in toluene (3.5 mL) was stirred at 40° C. for 24 h and at 6° C. for 1 h. The crystals were collected by filtration. The white crystalline product was washed with toluene (3×1 mL) and dried (vacuum, 30°–35° C., 2 h). The yield of N-(8-aminooctyl)-N'-benzyloxycarbonyl guanidine (IIIe) was 0.32 g (50% in theory).

1H NMR (CDCl$_3$): 7.33 (5H, Ph), 5.06 (2H, s, OCH$_2$Ph), 3.03 (2H, t, CH$_2$—N—C), 2.64 (2H, t, CH$_2$—NH$_2$), 1.2–1.4 (12H). Mp: 108°–112° C.

Example 23. N-(12-Aminododecyl)-N'-Benzyloxycarbonyl Guanidine

A mixture of N-benzyloxycarbonyl-O-methyl-isourea (II-OMe) (0.42 g, 2.0 mmol), toluene (3.5 mL) and 1,12- diaminododecane (If) (1.02 g, 5.0 mmol) was stirred at 40° C. for 12 h and at 20° C. for 1 h. The crystalline product was collected by filtration, washed with toluene (3×1 mL), and vacuum dried (35° C., 1.5 h) to afford 0.55 g (73%) of white crystals of N-(12-Aminododecyl)-N'-benzyloxycarbonyl guanidine (IIIf).

$^1$H NMR (CDCl$_3$): 7.36–7.28 (5H, Ph), 5.08 (2H, s, OCH$_2$Ph), 3.07 (2H,t,J=7.0, H-1), 2.66 (2H,t,J=7.0, H-12), 1.42–1.26 (16H,m,CH$_2$)

Example 24. N-(3-Aminopropyl)-N'-Tert-Butoxycarbonyl Guanidine

A mixture of tert-butoxycarbonyl-1-(3,5-dimethylpyrazolyl)-formamidine (0.38 g, 1.5 mmol) and 1,3-diaminopropane (0.56 g, 7.5 mmol) was stirred at room temperature for 17 h. The crystalline product was collected by filtration, washed with toluene (2×0.7) mL), and vacuum dried (35° C., 1.5 h) to afford 0.15 g (47%) of white crystals of N-(3-aminopropyl)-N'-tert-butoxycarbonyl guanidine (IIIg).

$^1$H NMR (CDCl$_3$): 3.33 (2H t, J=5.8, H-1, 2.80 (2H, t, J=6.0, H-3, 1.63 (2H, q, J=6.0, H-2), 1.44 (9H,s,CH$_3$ in Boc).

Preparation of Guanylation Reagents

Example 25. N-benzyloxycarbonyl 1-(3,5-Dimethylpyrazolyl) Formamidine (II-pyr)

To a stirred solution of sodium hydroxide (2.5 g, 62 mmol) and 3,5-dimethylpyrazolyl-1-formamidinium nitrate (5.0 g, 24.1 mmol) in water (60 mL) at 0° C. was added over a 10 minute period benzyl chloroformiate (4.35 g, 23.0 mmol). The cooling bath was removed and the reaction mixture was stirred at ambient temperature for 4.5 h. The crystalline product was collected by filtration, washed with cold water (2×20 mL), and vacuum dried (35° C., 26 h) to afford 4.34 g (69%) of white crystals of II-pyr.

NMR (CDCl$_3$); 7.4–7.3 (5H, Ph), 5.95 (1H, s, C=CH—C), 5.20 (2H, s, OCH$_2$Ph), 2.64 (3H, s, CH$_3$), 2.21 (3H, s, CH$_3$).

Example 26. N-Benzyloxycarbonyl-O-ethyl-isourea (II-OEt)

A mixture of N-benzyloxycarbonyl-O-methyl-isourea (II-OMe) (0.42 g, 2.0 mmol), ethanol (10 mL) and sulphuric acid, 95% (0.33 g, 5.8 mmol) was stirred at 40° C. for 14 h. The reaction mixture was filtrated, evaporated and eluated with 0, 1.25, 2.5, 5, 10, 20, 40, 80 and 100% ethylacetate/n-hexane through a silica gel column to afford 0.49 g (15%) of clear oil of II-OEt.

$^1$H NMR (CDCl$_3$): 7.40–7.30 (5H,Ph), 5.15 (2H,s, OCH$_2$Ph),4.32(2H, kv, J=7.2, OCH$_2$Me), 1.27 (3H, tr, J=7.1, CH$_3$)

Example 27. tert-Butoxycarbonyl-1-(3,5-Dimethylpyrazolyl)-Formamidine

To a stirred solution of sodium hydroxide (2.5 g, 62 mmol) and 3,5-dimethylpyrazolyl-1-formamidinium nitrate (5.0 g, 24.1 mmol) in water (60 mL) at 5° C. was added over a 1 minute period di-tert-butyl-carbonate (4.78 g, 21.9 mmol). The reaction mixture was stirred 4 h at 5° C. followed by stirring at room temperature over night. The reaction mixture was extracted with ethylacetate (2×25 mL), evaporated and eluated with 0, 1.25, 2.5, 5, 10, 20, 40, 80 and 100% ethylacetate/n-hexan through a silica gel column to afford 3.31 g (62%) of clear oil of tert-butoxycarbonyl-1-(3,5-dimethylpyrazolyl)-formamidine.

$^1$H NMR (CDCl$_3$): 2.62 (3H,s,CH$_3$), 2.19 (3H,s,CH$_3$), 1.50 (9H,s,CH$_3$)

The best mode to carrying out the invention known at present is to use the process described in Example 10.

The process of the invention is general and may be performed efficiently in one step yielding a product with high purity and in useful yields.

We claim:

1. A process for the production of a protected ω-aminoalkyl guanidine of the formula III, its tautomer or a salt thereof $$H_2N—C_nH_{2n}—NH—C(=NH)—NH—C(O)—O—R \quad (III)$$

which process comprises the step of reacting a diamine of the formula I $$H_2N—C_nH_{2n}—NH_2 \quad (I)$$

with a guanylation reagent of the formula II, its tautomer or a salt thereof $$ROC(O)—N=C(L)—NH_2 \quad (II)$$

in which formulae —$C_nH_{2n}$— is a linear or branched alkyl group wherein n is an integer of 2–18, R is selected from the group consisting of a linear or branched $C_1$–$C_{12}$-alkyl group and an aralkyl group, and L is a leaving group selected from the group consisting of a compound of the formula $R^2O$, $R^2S$, pyrazolyl and a substituted pyrazolyl, where $R^2$ is a lower alkyl group.

2. A process according to claim 1, wherein said $C_1$–$C_{12}$-alkyl group is a lower alkyl group.

3. A process according to claim 1, wherein said aralkyl group is a benzyl or substituted benzyl group.

4. A process according to claim 1, wherein —$C_nH_{2n}$— is a linear alkyl group where n is 2–12.

5. A process according to claim 1, wherein —$C_nH_{2n}$— is a linear alkyl group where n is 2–5, 8 or 12 and R is a t-butyl or benzyl group.

6. A process according to claim 5, wherein n is 3 and R is a benzyl group.

7. A process according to claim 1, wherein said reaction is performed in the absence of a solvent.

8. A process according to claim 1, wherein the reaction is performed in the presence of a solvent.

9. A process according to claim 8, wherein the reaction is performed in the presence of a solvent selected from the group consisting of an aromatic hydrocarbon, a hydrocarbon which is a linear or branched cyclic or acyclic hydrocarbon, an alkyl nitrile, an alcohol and water.

10. A process according to claim 9, wherein said aromatic hydrocarbon is an alkylbenzene selected from the group consisting of toluene and xylene.

11. A process according to claim 9, wherein said hydrocarbon is selected from the group consisting of hexane, heptane and cyclohexane.

12. A process according to claim 9, wherein said alkyl nitrile is acetonitrile.

13. A process according to claim 9, wherein said alcohol is isopropanol.

14. A process according to claim 1, wherein at least a stoichiometric amount of the diamine of formula I is present in relation to the guanylation reactant of formula II.

15. A process according to claim 14, wherein 1–10 mol equivalents of the diamine of formula I are present in relation to the guanylation reactant of formula II.

16. A process according to claim 15, wherein said diamine reactant of formula I is present in an amount of 1.5–6 mol equivalents in relation to the guanylation reactant of formula II.

17. A process according to claim 16, wherein said diamine reactant of formula I is present in an amount of 2–4 mol equivalents in relation to the guanylation reactant of formula II.

18. A process according to claim 1, wherein said reaction is performed at a reaction temperature of approximately 20°–80° C.

19. A process according to claim 18, wherein said reaction temperature is approximately 40°–60° C.

20. A process according to claim 1, wherein the compound of formula III is isolated by precipitation in the form of a crystalline product.

21. A process according to claim 20, wherein the compound of formula III is precipitated with an acid.

22. A process according to claim 21, wherein said acid is hydrochloric acid.

* * * * *